United States Patent [19]

Ison

[11] Patent Number: Plant 7,592

[45] Date of Patent: Jul. 16, 1991

[54] BLACK BEAUTY

[76] Inventor: William G. Ison, Rte. 1, Box 19, Hwy. 19, Brooks, Ga. 30205

[21] Appl. No.: 166,251

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Fry and the pollen parent variety 12-12-1 to produce an improved variety of muscadine grape.

1 Drawing Sheet

DESCRIPTION OF THE VARIETY

A cross between the female variety Fry and the pollen parent variety No. 12-12-1, a self-fertile variety which was never released or patented.

The primary objective of the breeding was to produce an improved variety of muscadine grape; which was to have superior characteristics for fresh fruit than either of its parents, these characteristics to include high quality, 100% dry scar for longer shelf life for fresh fruit, high sugar content; and the plant to be vigorous and productive.

In comparison with both the seed parent and the pollen parent, the new variety is similar in size to both the seed parent and pollen parent; but resembles in color the pollen parent. The fruit of this new variety contains on the average of 24% soluble solids, which sugar content is higher than both the parent plants. The present variety is a high yielding vine which yields on the average of six (6) to seven (7) tons per acre.

Asexual reproduction of the new variety either by soft-wood cuttings or by layering as performed at Brooks, Ga. shows that the foregoing characteristics and distinctions come true to form.

The accompanying photograph shows a typical specimen of the vegetative growth and fruit of the new variety when the fruit is ripe and ready for picking and as depicted in color as nearly true as it is reasonably possible to make the same in color illustration of the characters.

The following is a detailed description of the new variety:

Species: *Vitis rotundifolia.*

Seed parent: Variety Fry.

Pollen parent: Variety 12-12-1, self-fertile.

Propagation: Holds its characteristics through succeeding propagation by either layering or by soft-wood cuttings.

Locality where grown: Brooks, Ga.

Fruit:

*Borne.*—In clusters of approximately 5 to 18 berries per cluster.

*Size.*—Large, similar in size to the seed parent or larger; diameter 1" to 1¼".

*Color.*—Black, Black Group 202A Fan 4, The Royal Horticultural Society, London, England.

*Sugar content.*—Average 20% soluble solids.

*Shape.*—Round.

*Seed.*—Average diameter ⅛", average seed per berry 2½.

*Pulp.*—A. Color group green 195A Fan 4 The Royal Horticultural Society, London, England. B. Consistency, medium soft, medium juicy as compared to most muscadine varieties.

*Skin.*—Medium soft and edible.

Foliage:

*Leaf color.*—Green Group Fan 3 137B, The Royal Horticultural Society, London, England.

*Leaf size and shape.*—Similar to most muscadine varieties.

Reproductive organs: Pistillate-not self pollinating. Note: this is a female variety which can be reproduced from cuttings but when planted will not pollinate other varieties.

Growth habits: Very high vigor; vine requires support.

Canes: Medium to large caliper.

Maturity date: Usually ripens about September 25 at Brooks, Ga.

Diseases: Disease resistant.

This description was made from a muscadine vine grown at Ison's Nursery & Vineyards, Brooks, Ga.

I claim:

1. The new and distinct variety of grape plant as described and illustrated.

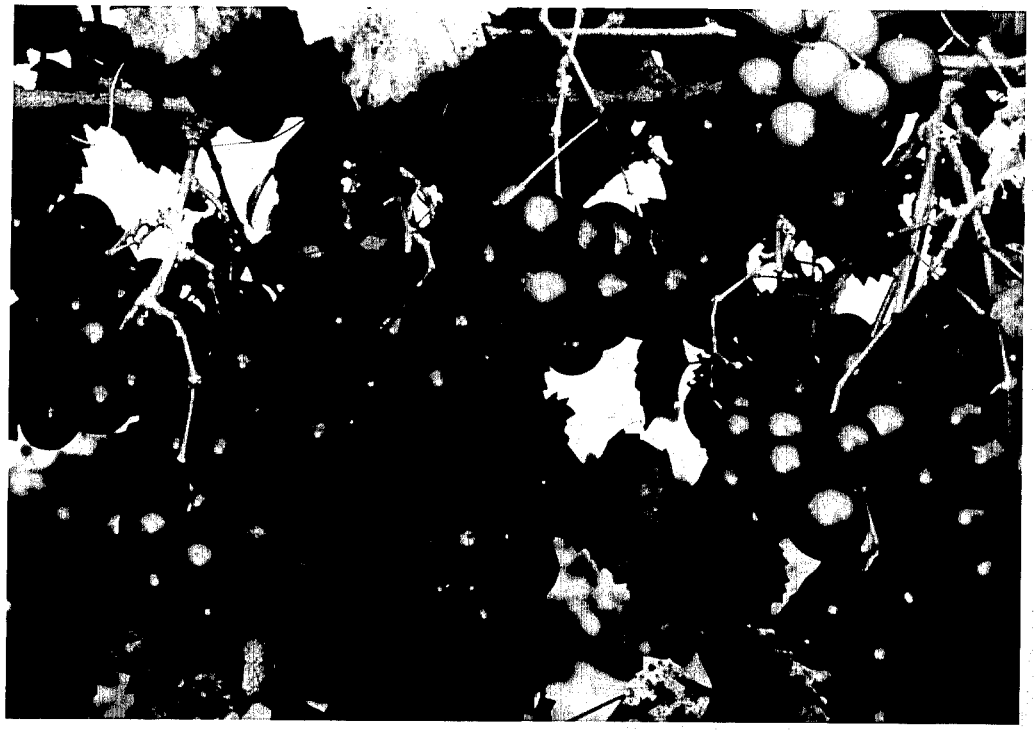

* * * * *